United States Patent [19]

Kiesele et al.

[11] Patent Number: 4,997,541

[45] Date of Patent: Mar. 5, 1991

[54] DOSIMETER HAVING A REUSABLE ELECTROCHEMICAL MEASURING CELL

[75] Inventors: Herbert Kiesele; Jürgen Tewes, both of Lübeck, Fed. Rep. of Germany

[73] Assignee: Drägerwerk Aktiengesellschaft, Lübeck, Fed. Rep. of Germany

[21] Appl. No.: 448,513

[22] Filed: Dec. 11, 1989

[30] Foreign Application Priority Data

Dec. 10, 1988 [DE] Fed. Rep. of Germany ....... 3841623

[51] Int. Cl.$^5$ .......................................... G01N 27/404
[52] U.S. Cl. .................................... 204/402; 204/415
[58] Field of Search .................. 204/402, 415; 422/88

[56] References Cited

U.S. PATENT DOCUMENTS

| | | | |
|---|---|---|---|
| 3,838,033 | 9/1974 | Mindt et al. | 204/415 X |
| 4,176,032 | 11/1979 | Stevenson | 204/415 |
| 4,267,023 | 5/1981 | Frant et al. | 204/415 X |
| 4,268,370 | 5/1981 | Neti | 204/415 |
| 4,545,382 | 10/1985 | Higgins et al. | 128/635 |
| 4,581,121 | 4/1986 | Dailey et al. | 204/406 |
| 4,711,245 | 12/1987 | Higgins et al. | 128/635 |
| 4,803,991 | 2/1989 | Alena et al. | 128/635 |
| 4,824,551 | 4/1989 | Rupich | 204/431 |

FOREIGN PATENT DOCUMENTS

446820 11/1974 U.S.S.R.

*Primary Examiner*—G. L. Kaplan
*Attorney, Agent, or Firm*—Walter Ottesen

[57] ABSTRACT

The invention is directed to a dosimeter for detecting gaseous substances or substances dissolved in liquids. The dosimeter includes a detection chamber which is partitioned off with respect to the ambient by a membrane which is permeable to the substance to be detected. The detection chamber is filled with an electrolyte which is subjected to changes in its characteristic under the action of the substance to be detected and these changes can be evaluated as electrical measured values via appropriate electrodes. The electrolyte contains a reagent which goes into an irreversible reaction with the substance to be detected and the dosimeter is improved so that after the evaluation it can be used again for measuring tasks or for collecting the substance to be detected. Furthermore, a calibration or a function test can be carried out on each dosimeter without its measurement readiness being limited thereby. A measuring electrode and a counter electrode are disposed in the detection chamber and are decoupled from each other with respect to a mass transport of the reagent as well as a reaction product formed from the reaction of the reagent with the substance to be detected. The reaction product can be converted quantitatively to a secondary product by a redox reaction at the measuring electrode by applying a voltage across the measuring electrode and the counter electrode.

10 Claims, 1 Drawing Sheet

DOSIMETER HAVING A REUSABLE ELECTROCHEMICAL MEASURING CELL

FIELD OF THE INVENTION

The invention relates to a dosimeter for detecting gaseous substances or substances dissolved in a liquid. The dosimeter includes a detection chamber which is closed off with respect to the ambient by a membrane permeable for the substance to be detected. The detection chamber is filled with an electrolyte which is subject to characteristic changes under the effect of the substance to be detected. The characteristic changes can be evaluated via corresponding electrodes as electrical measuring values with the electrolyte containing a reagent which goes into an irreversible reaction with the substance to be detected.

BACKGROUND OF THE INVENTION

Dosimeters are utilized to detect contaminants over long time durations and are used, for example, for monitoring a workplace. The dosimeters take up and collect the substance to be detected over the particular time duration so that the detected substance can be subjected to an evaluation at the end of the collection period.

A dosimeter of this kind is disclosed in U.S. Pat. No. 3,992,153. This dosimeter utilizes an oxidizing reagent for detecting nitrogen which stores the substance to be detected such as gaseous $NO_2$ by converting into $NO_3$-ions. For evaluation, ion-selective electrodes are introduced into the solvent and the collected ion concentration is determined by means of a voltage measurement. The quantity of the gaseous contaminant taken up during the collection time can be arrived at by conversion and inference.

Another dosimeter is described in copending application Ser. No. 341,579, filed on Apr. 21, 1989, which is incorporated herein by reference. This application discloses an electrochemical dosimeter by means of which substances can be detected via a conductivity measurement.

For the known dosimeter, it is disadvantageous that it cannot be utilized for further use after the evaluation. At least the electrolyte or the detecting solution must be exchanged for a new and unused one for which complex and carefully manipulated steps are required. Especially when filling the electrolyte chamber, care must be taken that the electrolyte quantity is very precisely measured because otherwise the measurements are not reproducible. Used dosimeters are destroyed since these steps, as a rule, cannot be carried out by operating personnel or the user. This leads to increased operating costs and to a burden for the environment because of the used solutions or electrolytes.

Dosimeters must be calibrated and their operating capability must be checked for a successful use thereof. For the known dosimeter, this can only be done in a random manner because each time the electrolyte solution is rendered unusable for measurement. The non-calibrated or non-tested dosimeters provided for measuring use can therefore only be evaluated on a probability basis.

SUMMARY OF THE INVENTION

It is an object of the invention to provide a dosimeter of the kind described above which is improved so that after its evaluation, it can again be used for measuring tasks and for collecting the substance to be detected. Furthermore, a calibration and a function test can be carried out for each dosimeter without its measuring readiness being restricted. The dosimeter is also intended for continuous measurements as required.

The dosimeter of the invention is for detecting a gaseous substance or a substance dissolved in a liquid. The dosimeter includes: a housing defining a detection chamber; a membrane closing off the chamber and being permeable to the substance to be detected; a measuring electrode disposed in the chamber; a counter electrode disposed in the chamber; an electrolyte disposed between the electrodes; a reagent contained in the electrolyte for entering into an irreversible reaction with the substance; the electrodes being decoupled from each other with respect to a mass transport of the reagent as well as a reaction product formed from the reaction of the reagent with the substance; and, voltage means for supplying a voltage across the electrodes to quantitatively convert the reaction product into a secondary product via a redox reaction at the measuring electrodes.

With the invention, the advantage is obtained that the reaction products formed during the collection phase can remain in storage until a voltage of a suitable polarity is applied to the electrodes which converts the formed products completely into secondary products. These formed secondary products do not participate in the further course of the reaction. The evaluation therefore at the same time means the renewal of the dosimeter so that it can be used directly for new measurement or collection tasks.

The dosimeter is also suitable for determining the slightest traces of gas quasi continuously since a coulometric evaluation and regeneration can be carried out in periodic time intervals after a collection time of several minutes.

A further advantage is that for large quantities of substance to be detected or when the collection over a longer time duration is not required or not desired, the dosimeter can be utilized as a continuous measuring device when the electrode voltage is applied.

A further advantage of the invention is seen in that a function test of the dosimeter can be carried out either before or after a collection operation of longer duration. For this purpose, the dosimeter is subjected to a known concentration of the substance to be detected and this is continuously measured. If the measuring current lies in the permitted error range, then the dosimeter can be used for collecting. If a calibration is required, then this can be undertaken and the dosimeter can continue to operate with the new calibration values.

An organic ammonium salt such as trishydroxymethylaminomethanehydrochloride can be utilized for determining ammonia. The hydrochloride reacts with the ammonia to form ammonium chloride and trishydroxylmethylaminomethane. The released amine can be coulometrically determined after the collection phase and converted to electrochemical inert final products so that the dosimeter is again available for new measuring and collection tasks.

It is especially advantageous to select a substance as a reagent which reacts with the substance to be detected to produce by means of the electrode reaction a final product which is again the reagent. Such a dosimeter is almost inexhaustible with respect to its reagent supply and is distinguished by a long service use. Potassium iodide dissolved in a phosphate buffer is especially well suited as such a reagent. This reagent is well suited for detecting chlorine. Furthermore, the potassium chloride leads to a blue coloration for the above-given reaction with the detection substance in the presence of starch. In this way, the person carrying the dosimeter can immediately recognize whether the substance to be detected is present and, if so, to judge from the degree of coloration in what amount the substance is present in order to initiate possible protective measures.

The electrolyte is preferably supplemented with the reagent in dissolved form and the decoupling with reference to the mass transport between the electrodes is effected by an ion exchanger membrane. The reagent is especially mobile in the dissolved form so that only a very thin reaction front can form on the membrane. This assures approximately constant mass transport conditions during the measuring time. The ion exchanger membrane makes possible, on the one hand, a rapid exchange of the conducting electrolyte and, on the other hand, prevents a penetration of the reaction products to the counter electrode and thereby prevents an unwanted change in the carrier exchange. A cationic exchanger on the basis of perfluorosulfonated PTFE has been found to be especially advantageous as a membrane material and is available in the marketplace under the trade name NAFION.

The ion exchanger membrane can preferably be either applied to the counter electrode at the electrolyte side or to the measuring electrode at the electrolyte side.

A further advantageous embodiment of the invention is obtained by providing a layer made of a conductive polymer on the measuring electrode. The detection substances diffusing through the membrane react with the polymer as a reagent and change the polymer structure via electron transfer. This step corresponds to the formation of an immobilized reaction product. After applying a voltage to the electrodes, the charge taken up is determined and the polymer is regenerated with the charge being a measure for the time-weighted concentration of the substance to be detected. Polyaniline has been found to be a suitable polymer.

The polymer in a matrix structure can be supplemented with catalysts to further increase the electrocatalytic activity. Such a catalytic substance is preferably ferrocene.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
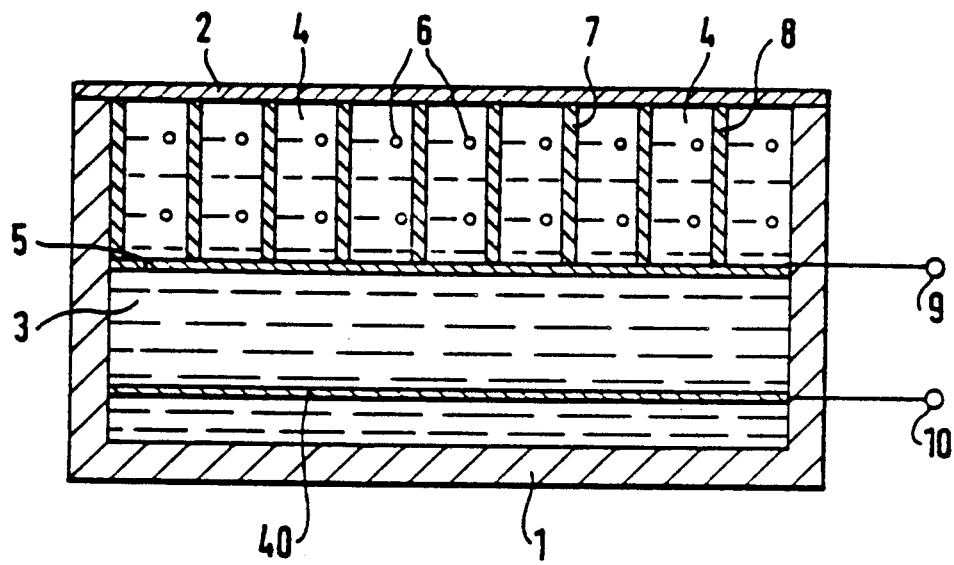
FIG. 1 is a schematic of an embodiment of the dosimeter according to the invention; and, FIG. 2 is a schematic of another embodiment of the dosimeter of the invention.

The components of the dosimeter shown in FIG. 1 are schematically represented and are not drawn to scale. The substance to be detected is in the ambient and the housing 1 defines a detection chamber which is partitioned from the ambient with the aid of a permeable membrane 2 which is welded to the peripheral edge of the housing 1. The inner chamber of the housing 1 is filled with an electrolyte 3 wherein a counter electrode 40 is accommodated in the housing and attached thereto.

An ion exchanger membrane 5 is also disposed in the electrolyte 3 and partitions the chamber toward the membrane 2 from the remaining space of the housing 1 wherein the counter electrode 40 is disposed. This chamber is filled with a reagent 6 dissolved in the electrolyte 3 and is illustrated with open circles. A measuring electrode 7 is also disposed in this chamber. The measuring electrode 7 has a honeycomb structure having webs 8 defining open pores. The open pores are closed off at one end by the permeable membrane 2 and at the other end by the ion exchanger membrane 5. The counter electrode 40 has a connection 10 and the measuring electrode 7 has a measuring connection 9 and both connections can be connected to a measuring and evaluation apparatus (not shown).

Figure 2:
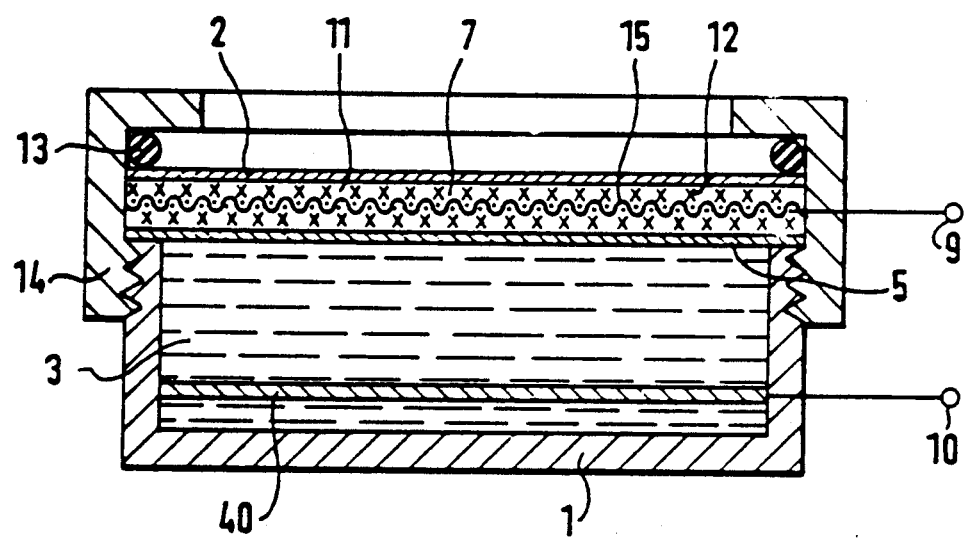

The embodiment shown in FIG. 2 likewise includes a housing 1 with an electrolyte 3 wherein the counter electrode 40 is disposed with its connection 10. The electrolyte 3 is partitioned off with an ion exchanger membrane 5. A layer of a conductive polymer 11 is disposed over the ion exchanger member 5 and this layer is supplemented with a catalyst 12 represented by crosses. The polymer layer 11 is tightly clamped between the membrane 2 and the ion exchanger membrane 5 with the aid of an 0-ring 13 and a threaded collar 14 on the housing 1 and is supported by means of a metal lattice 15. The metal lattice 15 and its measuring connection 9 together with the conductive polymer layer 11 conjointly define the measuring electrode 7.

It is understood that the foregoing description is that of the preferred embodiments of the invention and that various changes and modifications may be made thereto without departing from the spirit and scope of the invention as defined in the appended claims.

We claim:

1. A dosimeter for detecting a gaseous substance or a substance dissolved in a liquid, the dosimeter comprising:
    a housing having a detection chamber and an inner chamber;
    a membrane closing off said detection chamber from the ambient and being permeable to the substance to be detected;
    a measuring electrode disposed in said detection chamber;
    a counter electrode disposed in said inner chamber;
    an electrolyte disposed between said electrodes;
    a reagent disposed in said detection chamber for entering into an irreversible chemical reaction with said substance to form an electrochemically active intermediate product;
    barrier means for partitioning said housing into said chambers and for confining said reagent and said intermediate product to be in close proximity to said measuring electrode and to prevent an electrolytic exchange between said electrodes; and,
    voltage supplying means for supplying a voltage across said electrodes to quantitatively convert said intermediate reaction product into a final product via an electrochemical reaction at said measuring electrode.

2. The dosimeter of claim 1, said reagent being the chloride of trishydroxymethylaminomethane.

3. The dosimeter of claim 1, wherein said reaction product is converted into said final product in the form of said reagent.

4. The dosimeter of claim 1, said reagent being potassium iodide dissolved in phosphate buffer.

5. The dosimeter of claim 1, wherein said reagent and said substance conjointly form a colored reaction product.

6. The dosimeter of claim 1, said barrier means being an ion exchanger membrane arranged between said electrodes and said reagent being dissolved in the electrolyte.

7. The dosimeter of claim 1, said reagent being a layer of a conductive polymer on said measuring electrode.

8. The dosimeter of claim 7, said polymer being polyaniline.

9. The dosimeter of claim 8, comprising a catalyst added to said polymer.

10. The dosimeter of claim 9, said catalyst being ferrocene.

* * * * *